United States Patent [19]

Kaiser et al.

[11] 4,052,506

[45] Oct. 4, 1977

[54] PHARMACEUTICAL COMPOSITIONS AND METHOD OF PRODUCING ANTI-PARKINSONISM ACTIVITY

[75] Inventors: Carl Kaiser, Haddon Heights, N.J.; Robert G. Pendleton, Philadelphia; Paulette E. Setler, Fort Washington, both of Pa.

[73] Assignee: SmithKline Corporation, Philadelphia, Pa.

[21] Appl. No.: 602,042

[22] Filed: Aug. 5, 1975

[51] Int. Cl.² .............................................. A61K 31/33
[52] U.S. Cl. .................................................... 424/244
[58] Field of Search .................. 424/244; 260/239.3 B

[56] References Cited

U.S. PATENT DOCUMENTS

| | | | |
|---|---|---|---|
| 3,393,192 | 7/1968 | Walter et al. | 260/239.3 B |
| 3,609,138 | 9/1971 | De Stevens | 424/244 |
| 3,743,731 | 7/1973 | Walter et al. | 424/244 |
| 3,849,403 | 11/1974 | Yardley et al. | 260/239.3 B |

*Primary Examiner*—Stanley J. Friedman
*Attorney, Agent, or Firm*—Richard D. Foggio; William H. Edgerton

[57] ABSTRACT

Pharmaceutical compositions and method of producing anti-Parkinsonism activity by administering internally a nontoxic effective quantity of a benzazepine derivative to an animal.

10 Claims, No Drawings

PHARMACEUTICAL COMPOSITIONS AND METHOD OF PRODUCING ANTI-PARKINSONISM ACTIVITY

This invention relates to novel pharmaceutical compositions containing as an active ingredient compounds which have anti-parkinsonism activity and to a method of producing anti-parkinsonism activity by administering non-toxic effective quantities of said active ingredients to an animal.

Parkinson's disease is a neurological disorder characterized by hypokinesia, akinesia, tremor and rigidity of the limbs. Parkinsonism is believed to be brought about by imbalance in the biochemical systems in the brain between the dopaminergic and cholinergic neural pathways. In patients suffering from parkinsonism, a depletion of dopamine in the brain is observed which is the result of progressive degeneration of nigro-striatal dopaminergic neurons.

There is a great need for compounds and compositions which produce anti-parkinsonism activity without having limiting side effects. It is well known that L-dopa, a potential source of brain dopamine, has clinical utility in treating parkinsonism. L-Dopa is a precursor of dopamine, being decarboxylated in the brain, and thereby raising the levels of dopamine in patients who are deficient in it. However, L-Dopa does not qualify as an ideal compound in the treatment of parkinsonism due in part to its limiting side effects, such as, for example, nausea, emesis and anorexia.

It is therefore an object of the present invention to provide dopaminergic-like compounds having antiparkinsonism activity which do not possess the limiting side effects of L-dopa.

The active ingredients used in the compositions and methods of this invention are benzazepine derivatives represented by the following general structural formula:

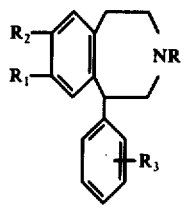

FORMULA I in which:

R is hydrogen, lower alkyl of from 1 to 4 carbon atoms, hydroxyethyl or lower alkenyl of from 3 to 5 carbon atoms, such as allyl or dimethylallyl;

$R_1$ is hydroxy, methoxy, ethoxy or alkanoyloxy;

$R_2$ is hydrogen, hydroxy, methoxy, ethoxy or alkanoyloxy; and $R_3$ is hydrogen, chloro, bromo, fluoro, methyl or trifluoromethyl, provided that when $R_1$ and $R_2$ are both methoxy or ethoxy, R is hydrogen, or a pharmaceutically acceptable acid addition salt of said compound.

The alkanoyl moieties advantageously have from 2 to 5 carbon atoms, such as acetyl, pivaloyl and the like.

Preferably R is hydrogen, methyl, ethyl or allyl, $R_1$ and $R_2$ are hydroxy and $R_3$ is hydrogen or a meta- or parasubstituent as defined above. Particularly advantageous compounds of formula I are 7,8-dihydroxy-1-phenyl-2,3,4,5-tetrahydro-1H-3-benzazepine and 7,8-dihydroxy-3-methyl-1phenyl-2,3,4,5-tetrahydro-1H-3-benzazepine.

The pharmaceutically acceptable acid addition salts having the utility of the free bases of formula I, prepared by methods well known to the art, are formed with both inorganic or organic acids, for example: maleic, fumaric, benzoic, ascorbic, pamoic, succinic, bismethylenesalicylic, methanesulfonic, ethanedisulfonic, acetic, oxalic, propionic, tartaric, salicyclic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

1-Phenyl-2,3,4,5-tetrahydro-1H-3-benzazepines have been described in U.S. Pat. No. 3,393,192; British Pat. Specification No. 1,118,688; and Swiss Pat. 555,831, including general methods of preparation. However, these references disclose very few specific compounds falling within the scope of formula I hereinabove. In addition there is no disclosure of the anti-parkinsonism properties of such compounds and their utility in the methods of this invention.

It will be obvious to one skilled in the art that the compounds of formula I may be present as diastereoisomers which may be resolved into d, 1 optical isomers. Resolution of the optical isomers may be conveniently accomplished by fractional crystallization of their salts with optically active acids from appropriate solvents. Unless otherwise specified herein or in the claims, it is intended to include all isomers, whether separated or mixtures thereof. Where isomers are separated, the desired pharmacological activity will usually predominate in one of the isomers.

The compounds of formula I where R is hydrogen are generally prepared from intermediates of the following formula:

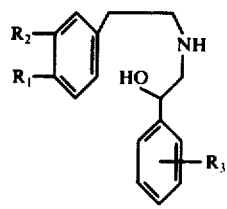

FORMULA II in which $R_1$ is methoxy or ethoxy; $R_2$ is hydrogen, methoxy or ethoxy; and $R_3$ is hydrogen, chloro, bromo, fluoro, methyl or trifluoromethyl; by means of an intramolecular cyclization effected by reaction with a reagent such as sulfuric acid, polyphosphoric acid or a similar dehydrating agent. To obtain the benzazepine products wherein $R_1$ and $R_2$ are hydroxy, cyclization of the corresponding methoxy substituted imtermediates is preferably carried out with 48% hydrobromic acid at reflux temperature for from two to four hours whereby simultaneous demethylation of the methoxy groups occurs.

Alternatively, the compounds of formula I where R is hydrogen may be prepared from 1-phenyl-2-oxo-2,3,4,5-tetrahydro-1H-3-benzazepine intermediates which are obtained by heating an appropriate phenylalkylamine with an ester of mandelic acid to give the amide. The latter is cyclized as described above to form the 2-oxobenzazepine intermediates which are chemically reduced, for example with borane in tetrahydrofuran, to the benzazepine products.

To prepare the compounds of formula I where R is lower alkyl, hydroxyethyl or lower alkenyl as defined above, the corresponding benzazepines where R is hydrogen are alkylated with ethylene oxide, or a lower alkyl or lower alkenyl bromide. Advantageously, to obtain the products where $R_1$ and/or $R_2$ are hydroxy the reaction with an alkyl bromide is carried out on the corresponding methoxy substituted benzazepines in an inert solvent such as methanol or acetone, preferably at reflux temperature and in the presence of a basic condensing agent such as potassium hydroxide or carbonate. Treatment of the resulting product with for example boron tribromide gives the hydroxy substituted benzazepines.

The compounds of formula I where R is methyl are conveniently prepared from methoxy substituted benzazepines wherein R is hydrogen by reaction with formic acid/formaldehyde. Similar treatment of the resulting product with boron tribromide gives the corresponding hydroxy substituted benzazepines.

To prepare the compounds of formula I where $R_1$ or $R_2$ is alkanoyloxy, the corresponding 3-benzyl-hydroxy-substituted benzazepine (obtained by alkylation of the hydroxy benzazepine with benzyl bromide in the presence of potassium carbonate) is treated with the appropriate alkanoic acid anhydride, for example acetic anhydride and the resulting alkanoyloxy substituted benzazepine is hydrogenated in the presence of palladium-on-carbon to remove the protective benzyl group.

The intermediates of formula II above are generally prepared by heating equimolar amounts of a styrene oxide with a phenethylamine, each appropriately substituted, either alone or in an inert organic solvent such as tetrahydrofuran. Preferably the heating is effected on a steam bath or at reflux temperature for from 12 to 24 hours. The required styrene oxide is conveniently prepared by reaction of the ylide derivative from sodium hydride and trimethylsulfonium iodide with the appropriate benzaldehyde.

The anti-parkinsonism activity of the benzazepine compounds of formula I which are the active ingredients used in accordance with the invention herein is demonstrated by employing a modified standard animal pharmacological test procedure reported by Ungerstedt et al., in Brain Research 24, 1970, 485–493. This procedure is based on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in this rat turning model. These compounds directly activate the dopamine receptors and cause contralateral rotation of the lesioned rat.

Rotational activity is defined as the ability of a compond to produce 500 contralateral rotations during a two-hour period after administration, usually intraperitoneally. The dose corresponding to 500 contralateral rotations per two hours is obtained and assigned as the $RD_{500}$ value.

An advantageous compound of formula I, 7,8-dihydroxy-1-phenyl-2,3,4,5-tetrahydro-1-H-3-benzazepine when tested as described above in rats produced an $ED_{500}$, i.p. of 1.2 mg/kg. Further this compound does not induce emesis or stereotyped behavior at doses which are effective in the rat turning model.

The compositions of this invention are prepared in conventional dosage unit forms by incorporating a compound in formula I or a pharmaceutically acceptable acid addition salt thereof, in a nontoxic amount sufficient to produce anti-parkinsonism activity in an animal, with a nontoxic pharmaceutical carrier according to accepted procedures. Preferably the compositions will contain the active ingredient in an active but nontoxic amount selected from about 25 mg. to about 100 mg. of active ingredient per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly, the carrier or diluent may include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing anti-parkinsonism activity in accordance with this invention comprises administering internally to an animal requiring said activity a compound of formula I or a pharmaceutically acceptable acid addition salt thereof, usually combined with a pharmaceutical carrier, in a nontoxic amount sufficient to produce said activity. The active ingredient will be administered preferably in a dosage unit, in an active, nontoxic quantity selected from about 25 mg. to about 100 mg. of the parent chemical of formula I. The route of administration may be orally or parenterally, the oral route being preferred. Advantageously, equal doses will be administered two or three times a day with the daily dosage regimen being selected from about 50 mg. to about 300 mg. When the method described above is carried out anti-parkinsonism activity is produced with a minimum of side effects.

The following examples illustrate specific pharmaceutical compositions and their use in accordance with the method of this invention and as such are not to be construed as limitations thereof.

EXAMPLE 1

| Ingredients | Mg. per Capsule |
| --- | --- |
| 7,8-Dihydroxy-1-phenyl-2,3,4,5-tetrahydro-1H-3-benzazepine (as an acid addition salt) | 25 (free base) |
| Magnesium stearate | 2 |
| Lactose | 200 |

The above ingredients are thoroughly mixed and placed into hard gelatin capsules.

EXAMPLE 2

| Ingredients | Mg. per Tablet |
| --- | --- |
| 7,8-Dihydroxy-1-phenyl-2,3,4,5-tetrahydro-1H-3-benzazepine (as an acid addition salt) | 100 (free base) |
| Corn starch | 15 |
| Polyvinyl pyrrolidinone | 6 |
| Corn starch | 8 |
| Magnesium stearate | 3 |

The first two ingredients are thoroughly mixed and granulated. The granules obtained are dried, mixed with the remaining corn starch and magnesium stearate, and compressed into tablets.

The capsules or tablets prepared as in Examples 1 or 2 are administered orally to an animal requiring antiparkinsonism activity within the dose ranges set forth hereinabove. Similarly, other compounds of formula I can be formulated in the same manner to give pharmaceutical compositions useful in the methods of this invention.

The following examples illustrate the chemical preparation of compounds of formula I and as such are not to be construed as limiting the scope thereof.

EXAMPLE 3

A mixture of 72 g. (0.4 mol) of 3,4-dimethoxyphenylethylamine and 48 g. (0.4 mol) of styrene oxide is heated on a steam bath under argon with stirring overnight. To the reaction mixture is added 200 ml. of 2:1/ethyl acetate: petroleum ether and seeded with N-[2-(3,4-dimethoxyphenylethyl]-2-phenyl-2-hydroxyethylamine. Stirring is continued for 15 minutes with chilling to crystallize N-[2-(3,4-dimethoxyphenyl)ethyl]2-phenyl-2-hydroxyethylamine, m.p. 94.5°-96° C.

A mixture of 100 g. (0.332 mol) of the above prepared ethylamine and 700 ml. of 48% hydrobromic acid is refluxed for two hours, cooling to room temperatue crystallizes the product, 7,8-dihydroxy-1-phenyl-2,3,4,5-tetrahydro-1H-3-benzazepine hydrobromide, m.p. 282°-283° C. Neutralization of the salt in water to which a trace of ascorbic acid has been added with alkali followed by ethyl acetate extraction furnishes the free base which can then be converted into other salts as described hereinabove.

EXAMPLE 4

A solution of 30.1 g. (0.1 mol) of N-[2-(3,4-dimethoxyphenyl)ethyl]-2-phenyl-2-hydroxyethylamine in 120 ml. of trifluoroacetic acid and 8.2 ml. of concentrated sulfuric acid is heated at reflux for two hours. After cooling to room temperature, the trifluoroacetic acid is removed under reduced pressure and 100 ml. of ice-water is added. This mixture is basified to pH 9-10 with 10% sodium hydroxide solution and thoroughly extracted with ethyl acetate. The extract is dried and evaporated to give 7,8-dimethoxy-1-phenyl-2,3,4,5-tetrahydro-1H-3-benzazepine as an oil. Various salts can readily be prepared from the free base. For example, 5 g. (0.0176 mol) dissolved in dry ether is treated with methanesulfonic acid dropwise until no further precipitate is formed. The solid is filtered and washed with dry ether to give 7,8-dimethoxy-1-phenyl-2,3,4,5-tetrahydro-1H-3-benzazepine methanesulfonate, m.p. 133°-136° C.

EXAMPLE 5

A 3.7 g. (0.0145 mol) sample of 7,8-dihydroxy-1-phenyl-2,3,4,5-tetrahydro-1H-3-benzazepine is slurried in 25 ml. of acetone and 0.7 g. (0.016 mol, 10% excess) of ethylene oxide is added. The mixture is placed in a pressure bottle and stirred at ambient temperature for about 40 hours. The reaction mixture is then heated to 60°-80° C. for 30 minutes, cooled and filtered. Concentration of the filtrate gives a solid which is taken up in ethyl acetate and reprecipitated with ether. The solid thus obtained is dissolved in ethanol and treated with ethereal hydrogen chloride to yield 7,8-dihydroxy-3-(2-hydroxyethyl)-1-phenyl-2,3,4,5-tetrahydro-1H-benzazepine hydrochloride, m.p. 136°-137° C.

EXAMPLE 6

A mixture of 42.0 g. of 57% sodium hydride dispersed in oil and 700 ml. of dimethyl sulfoxide is stirred at 70°-75° C. for one to one and one-half hours. The solution is diluted with 700 ml. of dry tetrahydrofuran and cooled to 0° C., under nitrogen. A 200 g. of (1.0 mol) sample of trimethylsulfonium iodide is added in portions, maintaining the temperature between 0°-5° C. The mixture is stirred for 15 minutes and then a solution of 70.4 g. (0.50 mol) of m-chlorobenzaldehyde in 300 ml. of dry tetrahydrofuran is added dropwise. The resulting mixture is stirred at room temperature for four hours, poured into water and extracted with ether. The extract is washed with brine, dried and evaporated in vacuo to leave m-chlorostyrene oxide.

A solution of 27.1 g. (0.1 mol) of N-benzyl-3,4-dimethoxyphenylethylamine and 23.3 g. (0.15 mol) of mchlorostyrene oxide in 500 ml. of methanol is stirred and refluxed overnight. The methanol is removed in vacuo and the residual N-benzyl-N-[2-(3,4-dimethoxyphenyl)ethyl]-2-hydroxy-2-(3-chlorophenyl)ethylamine is reduced without further purification. This sample (0.01 mol) is dissolved in ether, acidified and ethereal hydrogen chloride and the hydrochloride precipitates. The latter is dissolved in 90 ml. of methanol, the solution is added to a mixture of 0.5 g. of palladium-on-carbon in 10 ml. of ethyl acetate and the mixtue is hydrogenated at room temperature for 90 minutes at 60 psi. The reaction mixture is filtered and the filtrate evaporated in vacuo to yield N-[2-(3,4-dimethoxyphenyl)ethyl]-2-hydroxy-2-(3-chlorophenyl)ethyl-amine hydrochloride, m.p. 155°-157.5° C.

A solution of 6.0 g. (0.0161 mol) of the above prepared amine hydrochloride in 250 ml. of 48% hydrobromic acid is stirred and refluxed for three hours. The reaction mixture is evaporated in vacuo to give 1-(3-chlorophenyl)-7,8-dihydroxy-2,3,4,5-tetrahydro-1H-3-benzazepine hydrobromide, m.p. 231°-235° C.

EXAMPLE 7

Following the procedure of Example 6 and employing 42.0 g. of 57% of sodium hydride in mineral oil, 200 g. (0.1 mol) of trimethylsulfonium iodide and 70.4 g. (0.50 mol) of o-chlorobenzaldehyde there is a obtained o-chlorostyrene oxide.

Similarly 2.71 g. (0.01 mol) of N-benzyl-3,4-dimethoxyphenethylamine and 2.33 g. (0.015 mol) of o-chlorostyrene oxide are reacted in methanol to give N-benzyl-N-[2-(3,4-dimethoxyphenyl)ethyl]-2-hydroxy-2-(2-chlorophenyl)ethylamine. The latter is converted to its hydrochloride, which is dissolved in 90 ml. of methanol and hydrogenated over 1 g. of 10% palladium-on-carbon in 10 ml. of ethyl acetate at room temperature for six hours. The reaction mixture is filtered and evaporated in vacuo to leave N-[2-(3,4-dimethoxyphenyl)ethyl]-2-hydroxy-2-(2-chlorophenyl)ethylamine hydrochloride, m.p. 128°–132° C.

A solution of 3.84 g. (0.0103 mol) of the above hydrochloride in 250 ml. of 48% hydrobromic acid is stirred and refluxed for two hours. The reaction mixture is evaporated in vacuo to yield 1-(2-chlorophenyl)-7,8-dihydroxy-2,3,4,5-tetrahydro-1H-3-benzazepine hydrobromide m.p. 234°–235° C.

EXAMPLE 8

Following the procedure of Example 6 and employing 42.0 g. of 57% sodium hydride/mineral oil, 200 g. (1.0 mol) of trimethylsulfonium iodide and 70.4 g. (0.50 mol) of p-chlorobenzaldehyde there is obtained p-chlorostyrene oxide.

Similarly, 5.42 g. (0.02 mol) of N-benzyl-3,4-dimethoxyphenethylamine and 4.64 g. (0.03 mol) of p-chlorostyrene oxide are reacted in methanol to give N-benzyl-N-[2-(3,4-dimethoxyphenyl)ethyl]-2-hydroxy-2-(4-chlorophenyl) ethylamine. The hydrochloride of this ethylamine is dissolved in methanol and hydrogenated with 0.5 g. of 10% palladium-on-carbon in 10 ml. of ethyl acetate at room temperature and 60 psi. for about 90 minutes. The filtered reaction mixture is evaporated in vacuo to yield N-[2-(3,4-dimethoxyphenyl)ethyl]-2-hydroxy-2-(4-chlorophenyl)ethylamine hydrochloride, m.p. 167°–171° C.

A mixture of 5.0 g. (0.0134 mol) of this hydrochloride in 250 ml. of 48% hydrobromic acid is heated to reflux and then stirred and refluxed for 90 minutes. The reaction mixture is evaporated in vacuo to give 1-(4-chlorophenyl)-7,8-dihydroxy-2,3,4,5-tetrahydro-1H-3-benzazepine hydrobromide, m.p. 156°–164° C.

EXAMPLE 9

Sodium hydride (57% in mineral oil, 4.84 g., 0.115 mol) previously washed with hexene is stirred with 70 ml. of dimethylsulfoxide at 65°–70° C. for two hours under dry argon. The mixture is diluted with 70 ml. of dry tetrahydrofuran, cooled to −5° C. and 23.5 g. (0.115 mol) of trimethylsulfonium iodide in 100 ml. of dry dimethyl sulfoxide is added over a period of several minutes. After stirring for one minute, 11.9 g. (0.0926 mol) of mtolualdehyde is added at a moderate rate maintaining the temperature at 0° to −5° C. The mixture is stirred at 0° C. for five minutes and at ambient temperature for one hour, diluted with 500 ml. of ice-water and extracted with ether. The extract is washed with saturated sodium chloride solution, dried and evaporated to an oil, m-methylstyrene oxide.

A mixture of 14.5 g. (0.0797 mol) of 3,4-dimethoxyphenylethylamine and 10.7 g. (0.0797 mol) of m-methylstyrene oxide is stirred at 100° C. under argon for 16 hours and then diluted with benzene. Cooling in ice precipitates N-[2-(3,4-dimethoxyphenyl)ethyl]-2-hydroxy-2-(3-methylphenyl)ethylamine, m.p. 95.5°–97° C.

The above prepared ethylamine (9.6 g., 0.0304 mol) is refluxed in 65 ml. of 48% hydrobromic acid for two hours under argon. Cooling yields the product 7,8-dihydroxy-1-(3-methylphenyl)-2,3,4,5-tetrahydro-1H-3-benzazepine hydrobromide, m.p. 108°–110° C.

EXAMPLE 10

Following the procedure of Example 9 and employing a 57% dispersion sodium hydride in mineral oil (4.84 g., 0.115 mol), 23.5 g. (0.115 mol) of trimethylsulfonium iodide and 11.5 g. (0.0926 mol) of o-tolualdehyde there is obtained o-methylstyrene oxide.

Similarly a mixture of 13.6 g. (0.0753 mol) of 3,4-dimethoxyphenylethylamine and 10.1 g. (0.753 mol) of o-methylstyrene oxide is stirred at 100° C. under argon for 16 hours to yield N-[2-(3,4-dimethoxyphenyl)ethyl]-2-hydroxy-2-(2-methylphenyl)ethylamine, m.p. 91°–94° C.

The move prepared ethylamine (8.5 g., 0.0269 mol) is refluxed in 58 ml. of 48% hydrobromic acid for two hours under argon. Cooling precipitates the product, 7,8-dihydroxy-1-(2-methylphenyl)-2,3,4,5-tetrahydro-1H-3-benzazepine hydrobromide, m.p. 232°–233° C.

EXAMPLE 11

Following the procedure of Example 9 and employing 4.84 g. (0.115 mol) of a 57% dispersion of sodium hydride/mineral oil, 23.5 g. (0.115 mol) of trimethylsulfonium iodide and 11.9 g. (0.099 mol) of p-tolualdehyde there is obtained p-methylstyrene oxide.

Similarly a mixture of 10.6 g. (0.0789 mol) of p-methylstyrene oxide and 14.3 g. (0.0789 mol) of 3,4-dimethoxyphenylethylamine is stirred under argon and heated at 100° C. for 18 hours to yield N-[2-(3,4-dimethoxyphenyl)ethyl]-2-hydroxy-2-(4-methylphenyl)ethylamine, m.p. 99°–100° C.

The above prepared ethylamine (6.3 g., 0.02 mol) in 44 ml. of 48% hydrobromic acid is heated to reflux under argon for two and one-half hours. Cooling yields 7,8-dihydroxy-1-(4-methylphenyl)-2,3,4,5-tetrahydro-1H-3-benzazepine hydrobromide m.p. 261°–262° C.

EXAMPLE 12

A mixture of 20.0 g. (0.133 mol) of 4-methoxyphenylethylamine and 22.0 g. (0.133 mol) of methyl mandelate is heated at about 90° C. with stirring under nitrogen for 16 hours. The reaction mixture is taken up in ether from which the product, N-[2-(4-methoxyphenyl)ethyl]mandelamide, m.p. 86°–88° C., crystallizes.

The above prepared amide (30 g., 0.105 mol) is added in several portions to about 1 l. of polyphosphoric acid, freshly prepared from 660 g. of phosphorus pentoxide and 330 ml. of 85% phosphoric acid. The additions are made with stirring and with the polyphosphoric acid initially at a temperature of 90° C. Following addition the reaction mixture is stirred for our hour, poured into ice-water with stirring and the resulting solid filtered and dried to give 8-methoxy-2-oxo-1-phenyl-2,3,4,5-tetrahydro-1H-3-benzazepine, m.p. 155°–170° C.

The benzazepine (8.9 g., 0.033 mol) is added in small portions to 75 ml. of cold (0° C.) 1 M borane in tetrahydrofuran. The mixture is stirred under nitrogen, allowed to warm to ambient temperature and the resulting solution is refluxed for 18 hours. The reaction mixture is allowed to cool, about 50 ml. of methanol is added cautiously and the solution refluxed for one hour. A 20 ml. portion of dilute hydrochloric acid is added and the mixture is refluxed an additional hour. The solution is cooled, filtered and concentrated to give the solid reduced benzazepine, m.p. 150°-160° C.

This material (8.25 g.) is added with stirring to 100 ml. of 48% hydrobromic acid, the mixture is stirred under nitrogen and heated to reflux. Reflux is continued for three hours and the reaction mixture is allowed to cool, depositing a white crystalline solid. Filtration yields 8-hydroxy-1-phenyl-2,3,4,5-tetrahydro-1H-3-benzazepine hydrobromide, m.p. 229°-233° C.

EXAMPLE 13

A solution of 3.58 g. (0.0126 mol) of 7,8-dimethoxy-1-phenyl-2,3,4,5-tetrahydro-1H-3-benzazepine in 15 ml. of formic acid and 10 ml. of formaldehyde is refluxed for 18 hours. The reaction mixture is evaporated to dryness, 20 ml. of 6N hydrochloric acid is added and the solution is again evaporated to dryness to give a liquid. The latter is treated with 20 ml. of 10% sodium hydroxide solution and the mixture is extracted with ether. The dried extract is evaporated to give the liquid 7,8-dimethoxy-3-methyl-1-phenyl-2,3,4,5- tetrahydro-1H-3-benzazepine.

The above prepared 3-methyl benzazepine (2.6 g., 0.00875 mol) is dissolved in 120 ml. of dry methylene chloride and 6.8 g. (0.027 mol) of boron tribromide is added dropwise at −10° C. The resulting solution is warmed to room temperature and stirred for two hours. The excess boron tribromide is destroyed with methanol, added dropwise with ice-cooling. The solution is refluxed on the steam bath to remove hydrogen bromide and then evaporated to dryness to furnish 7,8-dihydroxy-3-methyl-1-phenyl-2,3,4,5-tetrahydro-1H-3-benzazepine hydrobromide, 247°-249° C.

EXAMPLE 14

A 3.78 g. (0.009 mol) sample of 3-benzyl-7,8-dihydroxy-1-phenyl-2,3,4,5-tetrahydro-1H-3-benzazepine (prepared from the 3-unsubstituted benzazepine by reaction with benzyl bromide in the presence of potassium carbonate) is dissolved in 50 ml. of acetic anhydride and the solution is heated on a steam bath for one hour. The reaction mixture is cooled, ice-water is added and the solution is evaporated to dryness. The residue is triturated with ethyl acetate, the solution washed with water, dried and the solvent removed in vacuo to leave an oil. The latter is dissolved in ether and ethereal hydrogen chloride is added to precipitate 3-benzyl-7,8-diacetoxy-1-phenyl2,3,4,5-tetrahydro-1H-3-benzazepine hydrochloride, m.p. 145°-150° C.

The diacetoxy compound prepared above, 3.5 g. (0.007 mol), is dissolved in 100 ml. of ethanol and 1 g. of 10% palladium-on-carbon is added. The mixture is hydrogenated in a Parr apparatus at 50° C. under 50 psi of hydrogen for one hour. The reaction mixture is filtered and the filtrate is evaporated to give 7,8-diacetoxy-1-phenyl-2,3,4,5-tetrahydro-1H-3-benzazepine hydrochloride, m.p. 170°-180° C.

EXAMPLE 15

A solution of 4.2 g. (0.01 mol) of 3-benzyl-7,8-dihydroxy-1-phenyl-2,3,4,5,-tetrahydro-1H-3-benzazepine in 20 ml. of pivalic anhydride is heated on a steam bath for four hours. The reaction mixture is cooled and excess ethereal hydrogen chloride is added followed by 200 ml. of ether to precipitate 3-benzyl-7,8-di(pivaloyloxy)-1-phenyl-2,3,4,5-tetrahydro-1H-3-benzazepine hydrochloride, m.p. 248°-250° C.

This compound (2.68 g.) is dissolved in 100 ml. of ethanol and 1.0 g. of 10% palladium-on carbon is added. The mixture is hydrogenated in a Parr apparatus at 37° C. under 50 psi of hydrogen for four hours. The reaction mixture is filtered and the filtrate is evaporated to dryness to yield 7,8-di(pivaloyloxy)-1-phenyl-2,3,4,5-tetrahydro-1H-3-benzazepine hydrochloride, m.p. 275°-276° C.

EXAMPLE 16

A sample of 7,8-dimethoxy-1-phenyl-2,3,4,5,-tetrahydro-1H-3-benzazepine weighing 4.32 g. (0.0154 mol), 2.18 g. (0.02 mol) of ethyl bromide and 1.12 g. (0.02 mol) of potassium hydroxide are dissolved in 120 ml. of dry methanol and the solution is refluxed overnight. Evaporation of the solution to dryness gives a mixture which is taken up in ethyl acetate and filtered to remove inorgaic salts. The filtrate is washed with water, dried and evaporated to give 7,8-dimethoxy-3-ethyl-1-phenyl-2,3,4,5-tetrahydro-1H-3-benzazepine as an oil.

The 3-ethyl benzazepine (3.32 g., 0.0107 mol) is dissolved in 120 ml. of dry methylene chloride and 8 g. (0.032 mol) of boron tribromide is added dropwise at −10° C. The solution is warmed to room temperature and stirred for two hours. The excess boron tribromide is destroyed with methanol added dropwise with ice-cooling. The cold solution is refluxed on the steam bath to remove hydrogen bromide and then evaporated to yield 7,8-dihydroxy-3-ethyl-1-phenyl-2,3,4,5-tetrahydro-1H-3-benzazepine hydrobromide, m.p. 263°-265° C.

EXAMPLE 17

Following the procedures of Example 16, an equimolar amount of n-propyl bromide is substituted for ethyl bromide to yield 7,8-dimethoxy-1-phenyl-3-n-propyl-2,3,4,5-tetrahydro-1H-3-benzazepine as an oil.

Subjecting this compound to the action of boron tribromide using the same molar quantities and experimental conditions described for the 3-ethyl derivative gives the product 7,8-dihydroxy-1-phenyl-3-n-propyl-2,3,4,5-tetrahydro-1H-3-benzazepine hydrobromide, m.p. 265°-267° C.

EXAMPLE 18

Substitution of an equimolar quantity of n-butyl bromide for the ethyl bromide of Example 16 and using the same experimental procedure described therein with the exception that the reflux period is increased to 48 hours gives 3-n-butyl-7,8-dimethoxy-1-phenyl-2,3,4,5-tetrahydro-1H-3-benzazepine as an oil.

Subjecting this compound to the action of boron tribromide using the same molar quantities and experimental conditions described for the 3-ethyl derivative furnishes the product 3-n-butyl-7,8-dihydroxy-1-phenyl-2,3,4,5-tetrahydro-1H-3-benzazepine hydrobromide, m.p. 231°-234° C.

EXAMPLE 19

A 3.3 g. (0.0129 mol) quantity of 7,8-dihydroxy-1-phenyl-2,3,4,5,-tetrahydro-1H-3-benzazepine is slurried in 40 ml. of dry acetone and 4.0 g. of anhydrous potassium carbonate is added. The mixture is stirred under nitrogen, a small amount of ascorbic acid is added as an antioxidant, the mixture is chilled to 0° C. and 1.57 g. (0.0129 mol) of allyl bromide is added. After stirring for two to three hours in the cold, the reaction mixture is allowed to warm to ambient temperature and stirred an additional 12 hours. The mixture is heated to reflux for 30 minutes, cooled, poured into water and extracted with ethyl acetate. Concentration of the extract gives a solid which is taken up in boiling ether and the solution is allowed to stand for several hours. The solution is filtered and ethereal hydrogen chloride is added to the filtrate to precipitate 3-allyl-7,8-dihydroxy-1-phenyl-2,3,4,5,-tetrahydro-1H-3benzazepine, hydrochloride, m.p. 232°–234° C. (dec.).

EXAMPLE 20

A mixture of 25 g. (0.0874 mol) of 2-methoxy-2(3-trifluoromethylphenyl)ethyl bromide and 75 ml. of 3,4-dimethoxyphenylethylamine is heated at 90°–95° C. for two hours with stirring under nitrogen. Cooling crystallizes 3,4-dimethoxyphenylethylamine hydrobromide which is filtered and the filtrate is fractionally distilled under vacuum. The fraction boiling at 207°–232° C. (1.3-2.0 mm.) is collected and treated with ethereal hydrogen chloride in ether solution to give N-[2-(3,4-dimethoxyphenyl)ethyl]-2-methoxy-2-(3-trifluoromethylphenyl)ethylamine hydrochloride, m.p. 157°–160° C.

A 1.0 g. (0.00238 mol) sample of this material is added to 20 ml. of 48% hydrobromic acid and the mixture is heated at reflux for one hour with stirring under nitrogen. The reaction mixture is cooled, concentrated to dryness under reduced pressure and the residue is triturated with ether to yield 7,8-dihydroxy-1-(3-trifluoromethylphenyl)-2,3,4,5-tetrahydro-1H-3-benzazepine hydrobromide, m.p. 153° C. (forms glass).

What is claimed is:

1. A method of producing anti-parkinsonism activity which comprises administering internally to an animal requiring said activity a nontoxic amount sufficient to produce said activity of a compound of the formula:

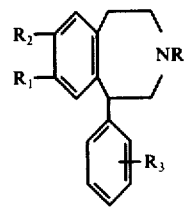

in which:
R is hydrogen, lower alkyl of from 1 to 4 carbon atoms, hydroxyethyl or lower alkenyl of from 3 to 5 carbon atoms;
$R_1$ is hydroxy, methoxy, ethoxy or alkanoyloxy;
$R_2$ is hydrogen, hydroxy, methoxy, ethoxy or alkanoyloxy;
$R_3$ is hydrogen, chloro, bromo, fluoro, methyl or trifluoromethyl; and
said alkanoyl moieties have from 2 to 5 carbon atoms, provided that when $R_1$ and $R_2$ are both methoxy or ethoxy, R is hydrogen, or a pharmaceutically acceptable acid addition salt of said compound.

2. The method of claim 1 in which R is hydrogen, methyl, ethyl or allyl, $R_1$ and $R_2$ are hydroxy, and $R_3$ is hydrogen or a meta- or para-substituent as defined above.

3. The method of claim 2 in which R and $R_3$ are hydrogen.

4. The method of claim 3 in which the compound is in the form of a free base.

5. The method of claim 3 in which the compound is in the form of a hydrobromide salt.

6. The method of claim 1 in which the active ingredient is administered with a pharmaceutical carrier in dosage unit form.

7. The method of claim 6 in which the administration is orally.

8. The method of claim 1 in which a daily dosage selected from the range of about 50 mg. to about 300 mg. of active ingredient is administered.

9. The method of claim 6 in which dosage units containing an active but nontoxic amount selected from about 25 mg. to about 100 mg. of active ingredient are administered two or three times a day.

10. The method of claim 1 in which R and $R_3$ are hydrogen, and $R_1$ and $R_2$ are acetoxy.

* * * * *